(12) United States Patent
Vaillancourt et al.

(10) Patent No.: US 8,905,944 B2
(45) Date of Patent: Dec. 9, 2014

(54) PROTECTIVE COVER ASSEMBLY FOR A NEEDLE ASSEMBLY

(75) Inventors: Michael J. Vaillancourt, Chester, NJ (US); Navdeep Athwal, West Caldwell, NJ (US)

(73) Assignee: VLV Associates, Inc., East Hanover, NJ (US)

( * ) Notice: Subject to any disclaimer, the term of this patent is extended or adjusted under 35 U.S.C. 154(b) by 357 days.

(21) Appl. No.: 13/585,058

(22) Filed: Aug. 14, 2012

(65) Prior Publication Data

US 2013/0324883 A1 Dec. 5, 2013

Related U.S. Application Data

(60) Provisional application No. 61/573,498, filed on Sep. 7, 2011.

(51) Int. Cl.
*A61B 10/02* (2006.01)
*A61M 25/00* (2006.01)

(52) U.S. Cl.
USPC ............. 600/567; 604/164.08; 604/263

(58) Field of Classification Search
CPC .................................................. A61M 25/0631
USPC .......... 600/566, 567, 576–579; 604/162, 163, 604/164.08, 171–172, 192, 198, 263; 606/170, 171
See application file for complete search history.

(56) References Cited

U.S. PATENT DOCUMENTS

| | | | | |
|---|---|---|---|---|
| 3,134,380 A | * | 5/1964 | Armao | 604/198 |
| 3,583,460 A | * | 6/1971 | Faust et al. | 138/89 |
| 4,564,054 A | * | 1/1986 | Gustavsson | 141/329 |
| 4,698,057 A | * | 10/1987 | Joishy | 604/176 |
| 4,725,267 A | * | 2/1988 | Vaillancourt | 604/192 |
| 4,850,976 A | * | 7/1989 | Heinrich et al. | 604/192 |
| 4,943,284 A | * | 7/1990 | Erlich | 604/263 |
| 4,978,344 A | * | 12/1990 | Dombrowski et al. | 604/198 |
| 5,234,411 A | * | 8/1993 | Vaillancourt | 604/171 |
| 5,295,972 A | * | 3/1994 | Mischenko | 604/192 |
| 5,312,371 A | * | 5/1994 | Dombrowski et al. | 604/198 |
| 5,630,803 A | * | 5/1997 | Tamaro | 604/263 |
| 5,685,860 A | * | 11/1997 | Chang et al. | 604/192 |

(Continued)

FOREIGN PATENT DOCUMENTS

WO WO 2005016419 2/2005

*Primary Examiner* — Max Hindenburg
*Assistant Examiner* — John Pani
(74) *Attorney, Agent, or Firm* — Francis C. Hand; Carella, Byrne, et al.

(57) ABSTRACT

In one embodiment, the protective cover assembly has a hub that is to be mounted on a needle assembly, such as a biopsy needle assembly, a cap that is movable off the hub to move over a cannula or stylet of the needle assembly and a pair of rolls of film within the cap. The rolls of film are secured at one end to the hub to unwind over the cannula. Pressing rolls or springs press the longitudinal edges of the film strips together in sealed relation to encase the cannula while the cap receives the end of the cannula or stylet in sealed relation. In a second embodiment, the cap is integrated with a hub of a needle assembly having a cannula extending from the hub.

21 Claims, 5 Drawing Sheets

(56) References Cited

U.S. PATENT DOCUMENTS

| | | | |
|---|---|---|---|
| 6,080,138 A * | 6/2000 | Lemke et al. | 604/263 |
| 6,986,759 B1 * | 1/2006 | Jeremijevic | 604/198 |
| 7,625,207 B2 * | 12/2009 | Hershey et al. | 433/91 |
| 2002/0065488 A1 * | 5/2002 | Suzuki et al. | 604/192 |
| 2003/0114797 A1 | 6/2003 | Vaillancourt | |
| 2005/0197627 A1 * | 9/2005 | Huang et al. | 604/171 |
| 2005/0245845 A1 * | 11/2005 | Roe et al. | 600/583 |
| 2011/0276013 A1 * | 11/2011 | Saitoh et al. | 604/263 |

\* cited by examiner

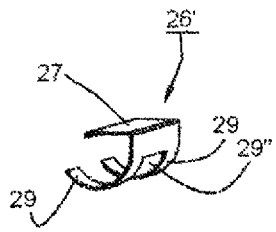
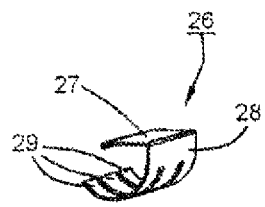
Fig. 17          Fig. 18
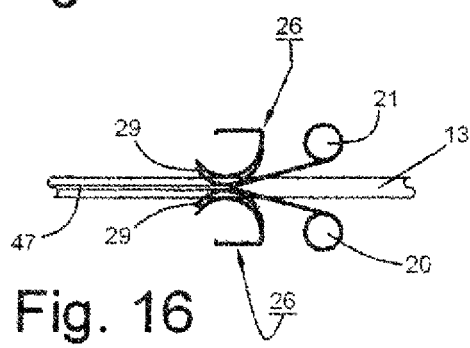
Fig. 16
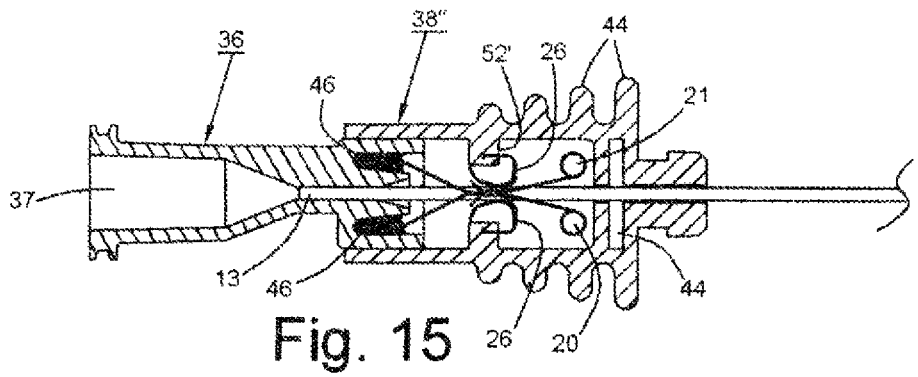
Fig. 15
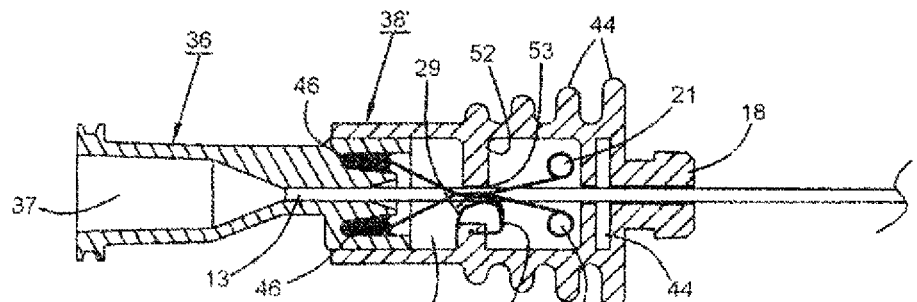
Fig. 14

PROTECTIVE COVER ASSEMBLY FOR A NEEDLE ASSEMBLY

This application claims the benefit of Provisional Patent Application 61/573,498, filed Sep. 7, 2011.

This invention relates to a protective cover assembly for a needle assembly. More particularly, this invention relates to a protective cover for a biopsy needle assembly.

As is known, various types of needle assemblies are employed in the medical field for various purposes. For example, biopsy needle assemblies are known for the taking of tissue specimens. Examples of such biopsy needle assemblies are described in U.S. Pat. Nos. 5,505,211; 5,538,010 and 5,578,030.

Generally, biopsy needle assemblies are constructed so that a stylet can be positioned in a patient in a manner to obtain a specimen of tissue as well as with a hollow cannula which is moveable relative to the stylet so that the stylet can be positioned within the cannula in order to prepare the tissue specimen for removal from the patient.

Once a biopsy needle assembly has been removed from the patient with a tissue specimen therein and the specimen removed for analysis, the biopsy needle assembly is discarded. However, the exposed cannula and/or stylet of the biopsy needle assembly presents a risk of "sticking" should a person come into contact with the stylet end of the discarded needle assembly.

Protective covers have been known for use with needles, such as the needle of a syringe, wire guide, biopsy needle and the like, such as described in published U.S. Patent Application 2003/0114797. As described therein, a cap is slidably mounted over a needle and tethered to a needle housing by a non-resilient tubular sheath of plastic which is concentrically disposed on and about the needle in a collapsed state. When the end of the needle is to be covered, the cap is pulled from the housing so that the sheath is longitudinally extended from the collapsed state to an extended state about the needle. As described, the sheath is characterized in having a low percentage of elongation to break that allows the sheath to be pulled out from the collapsed position to a slightly stretched condition to allow the cap to extend beyond the end of the needle. This allows a spring clip within the cap to slide off the needle and block re-entry of the needle through a bore in the cap through which the needle has passed. The cap is also allowed to retract under the force of the stretched sheath.

Other types of needle assemblies have been known with capping devices, such as described in U.S. Pat. No. 5,685,860.

Accordingly, it is an object of the invention to provide a protective cover assembly for a used needle assembly.

It is another object of the invention to provide a protective cover assembly which is simple to manipulate and to use for biopsy needle assemblies and the like.

It is another object of the invention to provide a protective cover assembly that can accommodate needles of relatively long length.

Briefly, the invention provides a protective cover assembly for a needle assembly that can be retro-fitted onto an existing needle assembly or fabricated integrally with a needle assembly.

The protective cover assembly is particularly adapted for use on a needle assembly wherein a cannula and stylet are movable relative to each other to position the stylet between an extended position outwardly of the cannula and a retracted position inwardly of the cannula.

As described in U.S. Pat. No. 5,538,010, a two piece biopsy needle is commonly employed for obtaining tissue core specimens and comprises a tubular cannula and a stylet located inside the cannula and movable relative to the cannula. The stylet is provided with a specimen notch on its periphery near a proximal tip of the stylet. In use, the biopsy needle is inserted through a small incision and driven into the body until its sharpened end enters the desired tissue to be sampled. During this insertion stage of the procedure, the stylet is positioned within the cannula so that no more than the sharp tip of the stylet is exposed; the specimen notch is covered by the cannula. Once the instrument has been positioned at the desired tissue, the stylet is driven into the tissue far enough to expose the specimen notch of stylet so that the soft tissue will then prolapse into the specimen notch. The cannula is then advanced along the stylet in order to cover the specimen notch while cutting out a specimen of the prolapsed tissue. With the cannula still concealing the specimen in the specimen notch, the biopsy needle assembly may then be withdrawn from the target site. Thereafter, the cannula is once again retracted in order to expose the specimen notch of the stylet, creating access to the tissue specimen contained therein.

As further described in U.S. Pat. No. 5,538,010, a spring loaded drive mechanism is provided to automate the operation of the biopsy needle assembly and particularly the back and forth motion of the cannula to produce the requisite sequential motion of the cannula and stylet.

In one embodiment, the protective cover assembly is constructed to be retrofitted onto a needle assembly as described above and comprises a hub, a hollow tube that extends from the hub and a cap that is mounted on the hub and disposed over the tube.

The hub of the protective cover assembly acts as an adapter so as to be mounted on the needle assembly. For example, the hub may be snap fitted or otherwise removably mounted on a housing of the needle assembly. Alternatively, the protective cover assembly may be manufactured in an integral manner to the needle assembly.

In any event, the hub is mounted on the needle assembly so that the cannula and stylet of the needle assembly extend through the hollow tube in a slide fit relation as well as through the cap that is mounted on the hub. With the protective cover assembly in place, the needle assembly can be manipulated in the usual manner for the purpose intended, for example, for obtaining a tissue specimen or used as a biopsy needle assembly, without interference from the protective cover assembly.

The cap is constructed with a bore for passage of the cannula and stylet of a needle assembly therethrough and is movable relative to the hub from a first position mounted on the hub to a second position spaced from the hub and disposed over the end of the cannula and stylet in sealed relation. After a tissue specimen has been obtained with the needle assembly for analysis and the needle assembly is ready to be discarded, the cap of the protective cover assembly is pulled manually from the hub and moved along the length of the cannula/stylet combination extending from the needle assembly until covering over the ends of the cannula and stylet.

The protective cover assembly also has a pair of rolls of film rotatably mounted within the cap. Each of these rolls of film has a free end secured to the hub whereby, as the cap is moved from the hub over the cannula/stylet combination, each roll of film unwinds in order to position a strip of film to opposite sides of the cannula/stylet combination extending from the needle assembly. In accordance with the invention, the strips of film are made to be self-adherent to each other.

In one embodiment, each roll of film is made of polyester film material with a medical grade adhesive applied to one side to form a sealable backing thereon facing the other roll of film.

The two strips of film upon being secured to each other provide for a secure encasement of the cannula and stylet. That is to say, the cannula and stylet are fully enclosed via the hub, cap and secured-together film strips.

Further, securement of the two strips of film together serves to rigidify the tethering of the cap to the hub of the cover assembly such that the cap cannot be retracted back towards the hub. In this respect, the securement of the two strips of film together provides a cross-sectional shape similar to a tube having two diametrically disposed outwardly extended flanges that resist buckling of the formed tube.

The protective cover assembly is also provided with means for pressing the two strips of film together in sealed relation about a cannula/stylet combination. In one embodiment, this pressing means includes a pair of rollers that are rotatably mounted in the cap downstream of the pair of rolls of film for pressing each strip of film to the other strip of film.

In another embodiment, the pressing means includes at least one spring mounted in the cap that has a pair of tines for pressing the longitudinal edges of at least one strip of film against the other strip of film.

Each roll of film is rotatably mounted in the cap on a fixed axis. Alternatively, each roll of film may be freely rotatably mounted in the cap with the cap being shaped to allow unwinding of the film as the cap moves away from the hub of the protective cover assembly.

The protective cover assembly may also be provided with suitable means to block passage of the cannula through the cap once the cap has been moved into place over the end of the cannula. Such a means may include a spring that is mounted in the cap adjacent to the bore through which the cannula passes and which has a pair of resilient legs that engage and slide along the cannula while the cap moves into position beyond the end of the cannula and which are moveable into a blocking alignment with the cannula in the extended position of the cap.

The cap is able to house rolls of film of different sizes for application over needles of different lengths. For example, a cap may accommodate rolls to form a protective cover over needles of a lengthy of from 6 cm to 40 cm.

In another embodiment, the protective cover assembly is fabricated integrally with a needle assembly having a hub and a needle that extends from the hub. In this embodiment, the protective cover assembly has a cap that is removably mounted on the hub and that is disposed to slide over the needle. The cap otherwise houses a pair of rolls of film and pressing means as in the first embodiment. In addition the free ends of the rolls of film are secured in the hub of the needle assembly such that the rolls of film are able to unwind as the cap is moved over the needle and away from the hub.

These and other objects and advantages of the invention will become more apparent from the following detailed description taken in conjunction with the accompanying drawings wherein:

FIG. 14 illustrates a cross-sectional view of a protective cover assembly in accordance with the invention with a modified pressing means;

FIG. 15 illustrates a cross-sectional view of a protective cover assembly in accordance with the invention with a further modified pressing means;

FIG. 16 illustrates another embodiment of a pressing means for securing each strip of film to the other strip of film in accordance with the invention;

FIG. 17 illustrates a perspective view of a spring used in the pressing means of FIG. 16; and FIG. 18 illustrates a modified spring for pressing the strips of film together in accordance with the invention.

Figure 1:
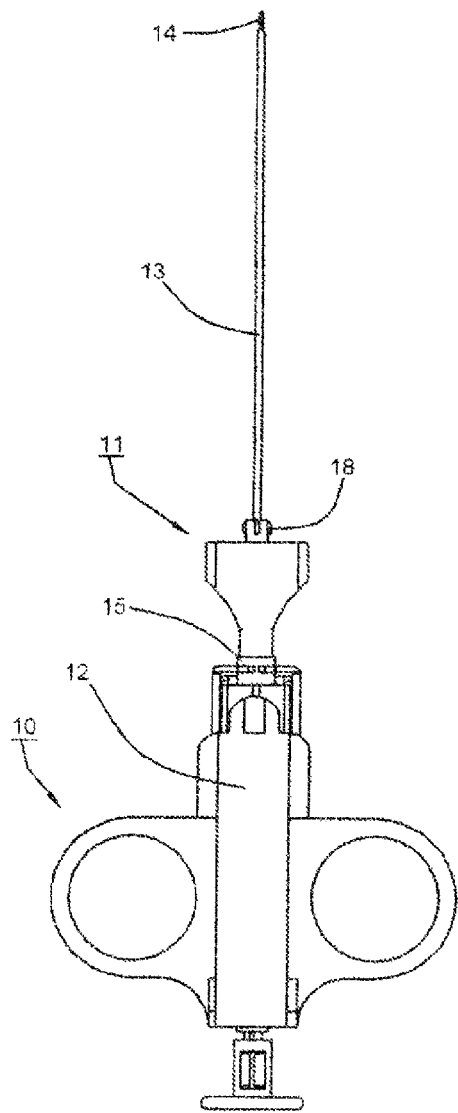
FIG. 1 illustrates a view of a biopsy needle assembly having a protective cover assembly in accordance with the invention.
Figure 2:
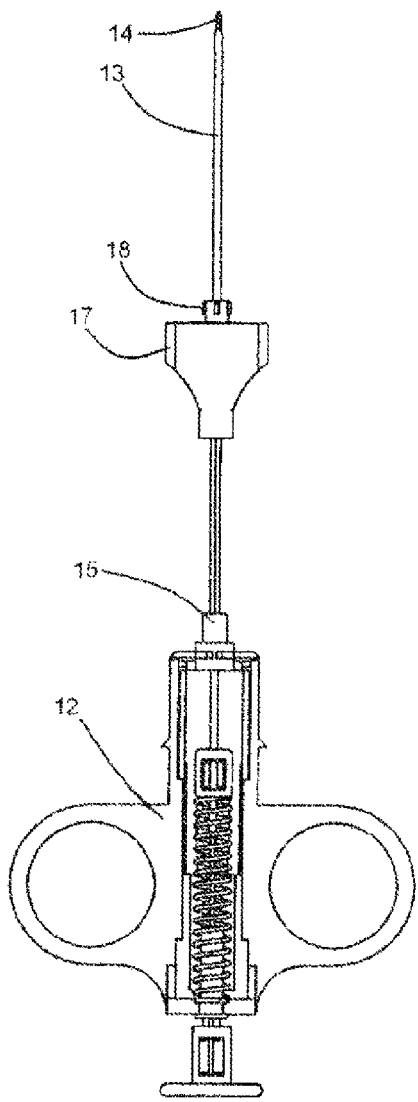
FIG. 2 illustrates a view similar to FIG. 1 during movement of the cap of the protective cover assembly towards an extended position in accordance with the invention.

Referring to FIGS. 1 and 2, a needle assembly 10 of conventional structure, is provided with a retro-fitted protective cover assembly 11 in accordance with the invention.

The needle assembly 10 is constructed with a housing 12, a hollow cannula 13 that extends from the housing 12 in known manner and a stylet 14 that extends within the cannula 13.

The needle assembly 10 is constructed so that the cannula 13 and stylet 14 are moveable relative to each other in order to position the stylet 14 between an extended position outwardly at the cannula and a retracted position with the tip of the stylet projecting slightly from the cannula 13. In this respect, the stylet 14 may be slidingly held in the cannula 13 in a manner as described in U.S. Pat. No. 5,578,030 or the cannula may be slid over the fixed stylet 14 to obtain a specimen in a manner similar to the biopsy needle described in U.S. Pat. No. 5,505,211. Also, the needle assembly 10 may be constructed with a spring loaded drive mechanism as described in U.S. Pat. No. 5,538,010.

Referring to FIG. 1, the protective cover assembly 11 has a hub 15 that is mounted on the housing 12 of the needle assembly 10. In this respect, the hub 15 may be snap fitted onto the housing 12 or may be otherwise removably mounted to the housing 12 so as to be retro-fitted onto the needle assembly 10. Alternatively, the protective cover assembly 11 may be integrally fabricated with the housing 12 of the needle assembly 10.

Figure 3:
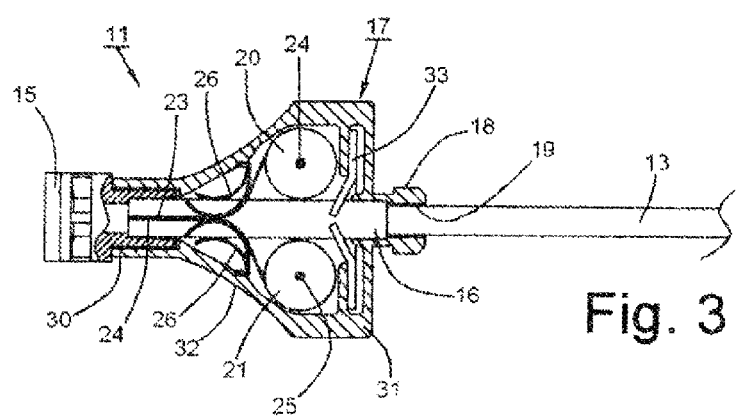
FIG. 3 illustrates a cross-sectional view of the protective cover assembly in accordance with the invention with a cannula of a needle assembly passing therethrough.

Referring to FIG. 3, the protective cover assembly 11 also has a hollow tube 16 that is mounted in the hub 15 in fixed relation and that extends from the hub 15 with the cannula 13 and stylet 14 (not shown) extending longitudinally therethrough. In this respect, the hollow tube 16 allows for relative longitudinal movement of the cannula 13 relative to the protective cover assembly 11 during use, for example, in obtaining a tissue specimen as described in U.S. Pat. No. 5,538,010.

The protective cover assembly 11 also has a cap 17 mounted on the hub 15 in slide fit relation. As illustrated, the cap 17 has an extension 18 with a bore 19 for passage of the cannula 13. As illustrated, the tube 16 extends from the hub 15 into the extension 18 of the cap 17.

Figure 5:
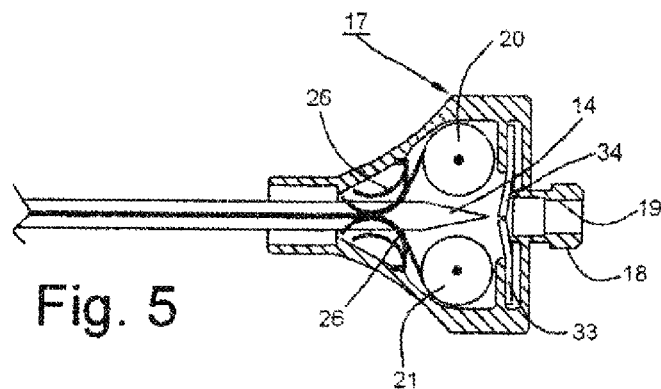
FIG. 5 illustrates a cross-sectional view of the cap of the protective cover assembly in a final extended position relative to the stylet of a needle assembly.

As indicated in FIGS. 1 and 2, the cap 17 is moveable relative to the hub 15 from a first position on the hub as shown in FIG. 1 to a second position (not shown) spaced from the hub 15 with the end of the stylet 14 disposed in the cap as illustrated in FIG. 5.

Figure 4:
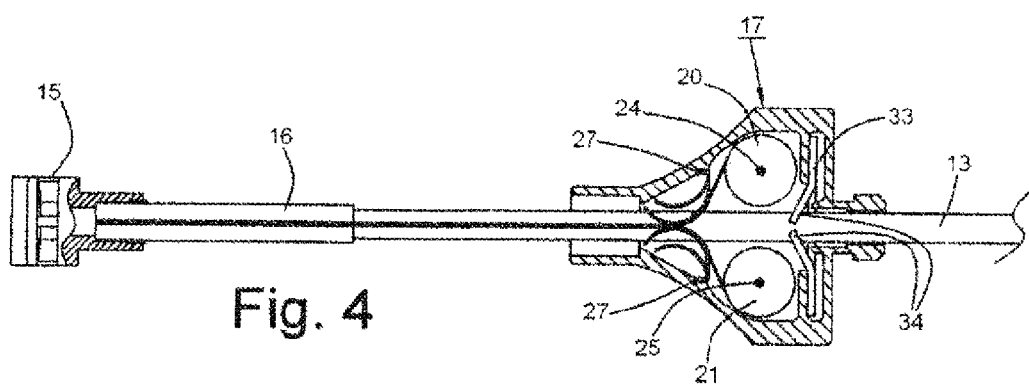
FIG. 4 illustrates a view of the protective cover assembly during movement of the cap of the assembly.

The cover assembly 11 also has a pair of rolls of film 20, 21 rotatably mounted within the cap 17. Each roll of film 20, 21 has one end secured to a spool on which the film is wound and a free end 22, 23 secured to the hub 15 in a suitable manner, such as by UV bonding, so that each roll of film 20, 21 unwinds in response to movement of the cap 17 from the position on the hub 15 to an extended position spaced from the hub 15 as indicated in FIGS. 4 and 5. During unwinding, each strip of film is positioned to opposite sides of the tube 16 and then the cannula 13. Upon complete unwinding, the strips of film 20, 21 stop the cap 17 from further movement. At this time, the stylet 14 is located in the cap 17 as illustrated in FIG. 5.

Referring to FIG. 3, each roll of film 20, 21 is made of a polyester film material with a sealable backing thereon disposed in facing relation to the other roll of film 20, 21. As the rolls of film 20, 21 unwind, the facing strips of film are aligned so as to come into face-to-face relation.

Each roll of film 20, 21 is freely mounted within the cap 17. Alternatively, each roll of film 20, 21 may be mounted on an axle 24, 25 that is rotatably mounted within the cap 17 on a fixed axis.

The cap 17 also houses a pressing means for pressing each strip of film to and against the other strip of film as well as against the cannula 13. As illustrated, the pressing means is constituted by two springs 26. As illustrated in FIG. 18, each spring 26 has a flat mounting portion 27 and a curvilinear portion 28 which is digitized to form three curved tines 29.

As illustrated in FIG. 4, the flat mounting portion 27 of each spring 26 is mounted in a slot within the cap 17. In addition, the two outermost tines 29 are biased towards the opposed spring 26 for pressing the longitudinal edges of the strips of film from the rolls 20, 21 against each other. The central most tine 29 is flexed against the tube 16 that extends from the hub 15. As the cap 17 moves away from the hub 15, the central most tine 29 of each spring 26 presses a strip of film against the cannula 13.

Referring to FIG. 3, the cap 17 includes a first portion 30 which is mounted on the hub 15, for example, in a slide fit manner. In addition, the cap 17 has a second portion 31 spaced from the first portion 30 to define a chamber that houses the two rolls 20, 21. In addition, the cap 17 has an inwardly curved portion 32 that extends to and between the first portion 30 and second portion 31 to define an exterior finger gripping surface.

Referring to FIG. 3, the cap 17 also has a spring 33 mounted in a recess adjacent to the bore 19. This spring 33 has a pair of resilient legs 34 that engage the tube 16 when the cap 17 is mounted on the hub 15. As the cap 17 is pulled from the hub 15, the legs 34 slide onto the cannula 13 as indicated in FIG. 4. After the cap 17 has been pulled beyond the stylet 14, the resilient legs 34 close on each other to move into blocking alignment with the stylet 14 thereby preventing the stylet 14 from moving out through the cap 17 as indicated in FIG. 5.

Referring to FIGS. 1 and 2, after the biopsy needle assembly 10 has been manipulated to obtain a tissue specimen and is ready for discarding, the cap 17 is manually pulled from the hub 15 and slid along the exposed cannula 13 as indicated in FIG. 2.

Referring to FIGS. 3, 4 and 5, as the cap 17 is pulled from the hub 15, the two rolls of film 20, 21 unwind so that two strips of film are played out over the cannula 13, while the pressing means 26 press the longitudinal edges of the strips together to form a tube having outwardly directed flanges formed thereon.

Referring to FIG. 5, each film 20, 21 is of a predetermined length so as to prevent the cap 17 from extending past the point of the stylet 14. Thus, as the cap 17 reaches the exposed end of the stylet 14, the motion of the cap 17 ceases and the legs 34 of the spring 33 flex inwardly to block re-entry of the stylet 14 through the bore 19 of the extension 18. At this time, the cannula 13 and stylet 14 are encased within the hub 15, the cap 17 and the sandwiched together strips of film. In addition, the strips of film become adhered to the surface of the cannula 13 thereby preventing a return motion of the cap 17 over the cannula 13.

Referring to FIGS. 6 to 10, wherein like reference characters indicate like parts as above, in another embodiment, the protective cover assembly 35 is integrated with a needle assembly 36 having a hub 37 from which a needle or cannula 13 extends.

Figure 6:
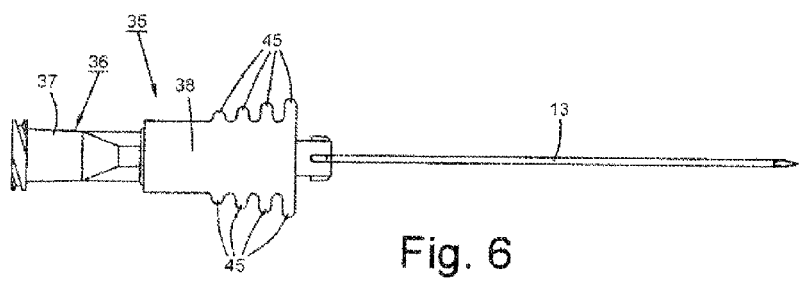
FIG. 6 illustrates a view of a protective cover assembly integrated with a needle assembly having a hub and a needle extending from the hub in accordance with the invention.
Figure 10:
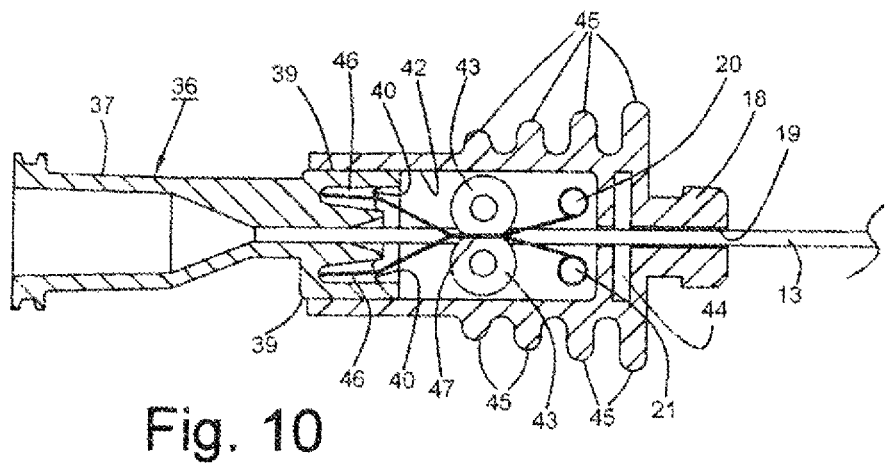
FIG. 10 illustrates an enlarged cross-sectional view of the protective cover assembly of FIG. 6.

Referring to FIGS. 6 and 10, the protective cover assembly 35 has a cap 38 of elongated shape that is slidably mounted on the hub 37 of the needle assembly.

Referring to FIG. 10, the hub 37 has a pair of flat exterior walls 39 on opposite sides of one end to slidingly receive the cap 38 and a pair of internal recesses 40 for purposes as explained below.

The cap 38 has a rectangular cross-section with a pair of flat exterior walls 41 (FIG. 7) and an open end compartment 42 at one end of rectangular cross-section that houses a pair of rolls of film 20, 21 as well as a pressing means in the from of a pair of compressible rolls 43. The opposite end of the cap 38 has an extension 18 with a bore 19 for passage of the cannula 13 or stylet (not shown) depending on the type of needle assembly on which the protective cover assembly 35 is mounted.

In addition, the cap 38 has a small compartment 44 adjacent the extension 18 for receiving a spring 33 (not shown) as above and a plurality of ribs 45 on two opposite sides to form finger-gripping surfaces.

The free end of each strip of film extending from the respective roll 20, 21 is fixed in a fitting 46 that is, in turn, anchored in a respective slot 40 of the hub 37. For example, each fitting 46 is in the form of a folded over element that clamps an end of a film strip therein. In addition, each fitting 46 is press-fit in a respective slot 40. Each fitting 46 may also be anchored in a slot 40 in any suitable manner.

Each roll of film 20, 21 is mounted on a fixed axis within the chamber 42 via an axle that is rotatably mounted in the side walls 41 of the cap 38 or via stub shafts at each end that are rotatably mounted in the side walls of the cap 38.

Each compressible roll 43 is mounted on a fixed axis in the cap 38 in similar manner to the rolls of film 20, 21.

As shown in FIG. 10, the strip of film from each roll 20, 21 is deflected about a respective compressible roll 43 and the two opposed strips of film are pressed together upon passing between the two compressible rolls 43. During passage, the longitudinal edges of the two strips of film are pressed together to form a flange 47 on each diametric side of the secured together strips of film (see FIG. 7).

Figure 8:
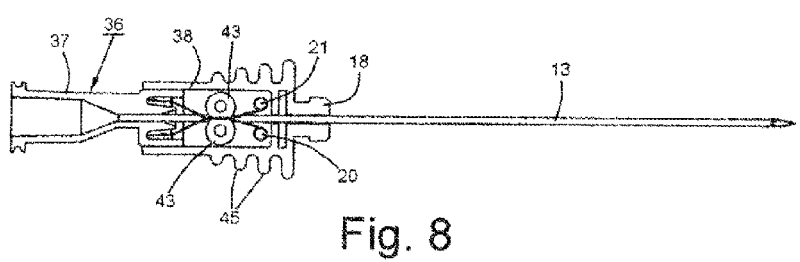
FIG. 8 illustrates a cross-sectional view of the protective cover assembly of FIG. 6.

Referring to FIGS. 6 and 8, in use, the protective cover assembly 35 is mounted in a fixed manner via the cap 38 on the hub 37 of the needle assembly 36 with the cannula 13 (or needle) of the needle assembly 36 extending through the protective cover assembly 35.

Figure 9:
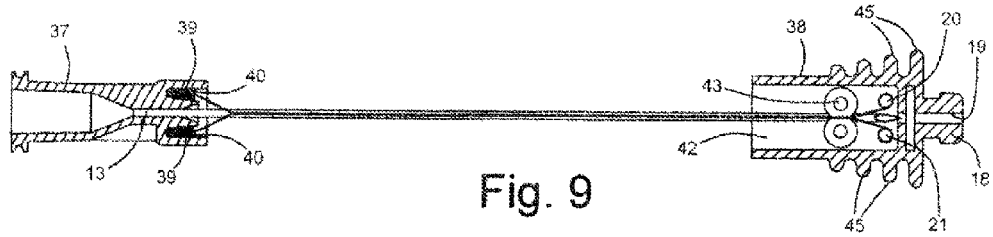
FIG. 9 illustrates a cross-sectional view of the protective cover assembly in the protective state of FIG. 7.
Figure 7:
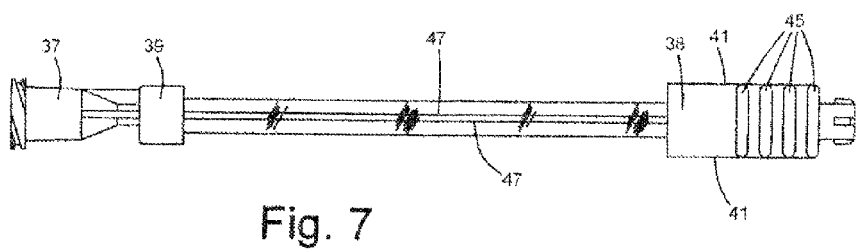
FIG. 7 illustrates a view of the protective cover assembly of FIG. 6 in a protective state over the end of a needle.

After the needle assembly has been used for the purpose intended and is ready to be discarded or otherwise set aside, the cap 38 is pulled from the hub 37 from the position of FIGS. 6 and 8 to the position of FIGS. 7 and 9. During this time, the rolls 20, 21 of film unwind while the compressible rolls 43 press the strips together into sealed relation to each other about the cannula 13 (or stylet) to sandwich the cannula 13 (or stylet) therebetween.

As above, each film 20, 21 is of a predetermined length so as to prevent the cap 38 from extending past the end of the cannula 13. Thus, upon reaching the position indicated in FIG. 9, the motion of the cap 38 ceases and the end of the cannula 13 is positioned within the compartment 42 of the cap 38 and the resilient legs 34 of the spring 33 (not shown) are biased inwardly, such as shown in FIG. 5, to block passage of the cannula 13 through the extension 18 of the cap 38.

Figure 11:
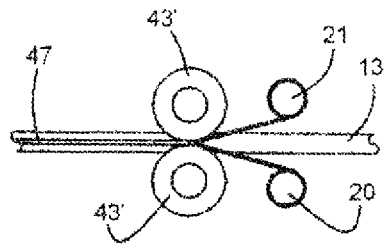
FIG. 11 illustrates a partial view of a pressing means for securing two strips of film together in accordance with the invention.

Referring to FIG. 11, wherein like reference characters indicate like parts as above, the pressing means may be in the form of a pair of non-compressible rolls 43'.

Figure 13:
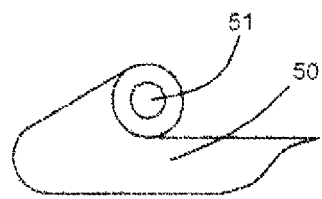
FIG. 13 illustrates a modified roll of film employed in accordance with the invention.
Figure 12:
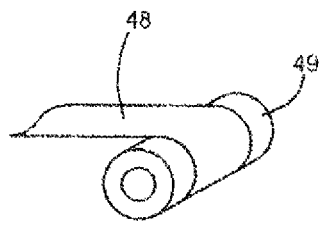
FIG. 12 illustrates a perspective view of a roll of film employed in accordance with the invention.

Each roll 20, 21 of film may be formed of a strip of film 48 that is of a width smaller than a mounting sleeve 49 on which the strip 48 is wound as shown in FIG. 12 or may be formed of a strip of film 50 that is of the same width as a mounting axle 51 on which the strip 50 is wound as shown in FIG. 13.

Referring to FIG. 14, wherein like reference characters indicate like parts as above, a single spring 26 may be used for pressing the longitudinal edges of the strips of film together. In this respect, the cap 38' includes an internal wall 52 within the compartment 42 that has an opening 53 through which the tube 16 passes and through which the two strips of film are passed from the rolls 20, 21.

As illustrated, a single spring 26 is mounted in the wall 52 with the tines 29 projecting into the opening 53 in the wall 52.

As shown, the free ends of the strips of film from the rolls 20, 21 are secured in the fittings 46 anchored in the slots 40 of the hub 37. The length of each strip between a fitting 46 and a roll 20, 21 is deflected in order to pass through the opening 53 in the wall 52 and is positioned between the cannula 13 and the wall 52. The lowermost strip of film rests against the spring 26 with the resilient tines 29 of the spring 26 pushing the lowermost strip against the uppermost strip of film.

During assembly, each roll of film is pre-loaded onto the cannula 13 then dropped into the cap 38. A cover that forms part of the cap is then welded on to cover the internal rollers and springs.

As the cap 38' is slid off the hub 36, the rolls 20, 21 of film unwind. During this time, as the wall 52 of the cap 39' moves along the cannula 13 the spring 26 presses the lower-most strip against the upper-most strip of film to secure the longitude edges of the film together.

Referring to FIG. 15, wherein like reference characters indicate like parts as above, the cap 38" has an internal wall 52" with an enlarged opening 53" and a pair of springs 26 are used to press the longitudinal edges of the opposed films together in a manner as in the embodiment of FIG. 3.

Referring to FIG. 16, as is the case shown in FIG. 11, the outermost tines 29 of the springs 26 resiliently deflect to press the longitudinal sides of the two strips of film together to form flanges 47.

Referring to FIG. 17, wherein like reference characters indicate like parts as above, a pressing spring 26" may be modified so that the central tine 29" is shortened relative to the outer-most tines 29 so as to accommodate passage over a cannula (not shown).

The invention thus provides a protective cover assembly that can be retrofitted onto a needle assembly, such as a biopsy needle, in order to close off the end of the needle assembly when the needle assembly is being discarded after use or may be integrated with a needle assembly having a hub from which a needle extends.

The protective cover assembly is constructed in a universal manner so as to be used with needle assemblies having different lengths of projecting needles as well as different diameters of projecting needles (or cannulae).

What is claimed is:

1. A protective cover assembly comprising
a hub;
a hollow tube extending from said hub;
a cap mounted on said hub and disposed over said tube, said cap having a bore for passage of said tube therethrough and being movable relative to said tube from a first position mounted on said hub to a second position spaced from said hub and said tube; and
a pair of rolls of film rotatably mounted within said cap, each said roll of film having a free end secured to said hub whereby each said roll of film unwinds in response to movement of said cap from said first position to said second position to position a strip of film from each said roll of film in facing relation to the other strip of film.

2. A protective cover assembly as set forth in claim 1 wherein each said roll of film is made of polyester film material.

3. A protective cover assembly as set forth in claim 1 wherein each said roll of film has a sealable backing thereon facing the other of said rolls of film.

4. A protective cover assembly as set forth in claim 3 further comprising pressing means for pressing each said strip of film to the other said strip of film.

5. A protective cover assembly as set forth in claim 4 wherein said pressing means includes a pair of rollers rotatably mounted in said cap downstream of said pair of rolls for pressing each said strip of film to the other said strip of film.

6. A protective cover assembly as set forth in claim 4 wherein said pressing means includes at least one spring mounted in said cap downstream of said pair of rolls and having a pair of tines for pressing the longitudinal edges of at least one said strip of film against the other said strip of film.

7. A protective cover assembly as set forth in claim 1 wherein each said roll of film is rotatably mounted in said cap on a fixed axis.

8. A protective cover assembly as set forth in claim 1 wherein each said roll of film is freely rotatably mounted in said cap.

9. A protective cover assembly as set forth in claim 1 wherein said cap includes a plurality of raised ribs thereon to define a finger-gripping portion.

10. A protective cover assembly as set forth in claim 1 wherein said cap includes a first portion mounted on said hub, a second portion spaced from said first portion and defining a chamber housing said pair of rolls and an inwardly curved portion extending to and between said first portion and said second portion to define an external finger-gripping surface.

11. A protective cover assembly comprising
a cap having a bore for passage of a cannula therethrough and being movable relative to the cannula from a first position mounted on the cannula to a second position at an end of the cannula; and
a pair of rolls of film rotatably mounted within said cap for unwinding in response to movement of said cap from said first position to said second position to position a strip of film from each said roll of film in facing relation to the other strip of film; and
pressing means mounted within said cap for pressing each said strip of film to the other said strip of film.

12. A protective cover assembly as set forth in claim 11 wherein each said roll of film has a sealable backing thereon facing the other of said rolls of film.

13. In combination
a biopsy needle having a housing, a hollow cannula extending from said housing and a stylet extending within said cannula, said cannula and said stylet being movable relative to each other to position said stylet between an extended position outwardly of said cannula to contact tissue and a retracted position inwardly of said cannula to retain a specimen of the tissue therebetween; and
a protective cover assembly for said biopsy needle having a hub mounted on said housing, a hollow tube extending from said hub with said cannula and said stylet extending longitudinally therethrough, a cap mounted on said hub and having a bore for passage of said cannula and said stylet therethrough and being movable relative to said hub from a first position on said hub to a second position spaced from said hub with an end of said cannula disposed in said cap in spaced relation to said bore, and a pair of rolls of film rotatably mounted within said cap, each said roll of film having a free end secured to said hub whereby each said roll of film unwinds in response to movement of said cap from said first position to said second position to position a strip of film from each said roll of film to opposite sides of said cannula.

14. The combination as set forth in claim 12 wherein each said roll of film has a sealable backing thereon facing the other of said rolls of film.

15. The combination as set forth in claim 14 further comprising means for pressing each said strip of film to the other said strip of film into sealed relation about said cannula.

16. The combination as set forth in claim 14 further comprising means disposed in said cap for selectively sealing off said bore to the passage of said cannula therethrough.

17. In combination
a needle assembly having a hub and a cannula extending from said hub; and
a protective cover assembly for said needle assembly having a cap removably mounted on said hub and having a bore for passage of said cannula therethrough and being movable relative to said hub from a first position on said hub to a second position with an end of said cannula disposed in said cap in spaced relation to said bore, and a pair of rolls of film rotatably mounted within said cap, each said roll of film having a free end secured to said hub whereby each said roll of film unwinds in response to movement of said cap from said first position to said second position to position a strip of film from each said roll of film to opposite sides of said cannula.

18. The combination as set forth in claim 17 wherein each said roll of film has a sealable backing thereon facing the other of said rolls of film.

19. The combination as set forth in claim 17 further comprising pressing means for pressing each said strip of film to the other said strip of film into sealed relation about said cannula.

20. The combination as set forth in claim 17 further comprising means disposed in said cap for selectively sealing off said bore to the passage of said cannula therethrough.

21. The combination as set forth in claim 17 further comprising a spring mounted in said cap adjacent said bore thereof and having a pair of resilient legs engaging said cannula in said first position of said cap and being movable into blocking alignment with said stylet in said second position of said cap.

* * * * *